(12) United States Patent
Diebold et al.

(10) Patent No.: US 9,423,353 B2
(45) Date of Patent: Aug. 23, 2016

(54) APPARATUS AND METHODS FOR FLUORESCENCE IMAGING USING RADIOFREQUENCY-MULTIPLEXED EXCITATION

(71) Applicant: THE REGENTS OF THE UNIVERSITY OF CALIFORNIA, Oakland, CA (US)

(72) Inventors: Eric D. Diebold, Los Angeles, CA (US); Bahram Jalali, Los Angeles, CA (US); Brandon Buckley, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/792,282

(22) Filed: Jul. 6, 2015

(65) Prior Publication Data

US 2016/0003741 A1  Jan. 7, 2016

Related U.S. Application Data

(63) Continuation of application No. PCT/US2014/010928, filed on Jan. 9, 2014.

(60) Provisional application No. 61/750,599, filed on Jan. 9, 2013.

(51) Int. Cl.
*G01N 21/64* (2006.01)
*G02B 21/16* (2006.01)

(52) U.S. Cl.
CPC ........ *G01N 21/6458* (2013.01); *G01N 21/6486* (2013.01); *G02B 21/16* (2013.01); *G01N 2021/6419* (2013.01); *G01N 2201/06113* (2013.01)

(58) Field of Classification Search
CPC ............................ G01N 21/6458; G02B 21/16
USPC ...................................................... 250/459.1
See application file for complete search history.

(56) References Cited

U.S. PATENT DOCUMENTS 5,296,911 A * 3/1994 Weyrauch ............ G01N 21/253
356/328
6,057,814 A * 5/2000 Kalt ....................... G02B 26/02
345/31

(Continued)

FOREIGN PATENT DOCUMENTS

JP          11-006719 A      1/1999

OTHER PUBLICATIONS

Korea Intellectual Property Office (KIPO), international search report and written opinion, PCT/US2014/010928, issued May 1, 2014, pp. 1-12, with claims searched, pp. 13-17, counterpart to U.S. Appl. No. 14/792,282. The degree of relevance of the three non-English language references listed above is set forth in this English-language search report and, therefore, a separate concise explanation to of the relevance of each reference is not required.

*Primary Examiner* — David Porta
*Assistant Examiner* — Abra Fein
(74) *Attorney, Agent, or Firm* — O'Banion & Ritchey LLP; John P. O'Banion

(57) ABSTRACT

Apparatus and methods for fluorescence imaging using radiofrequency multiplexed excitation. One apparatus splits an excitation laser beam into two arms of a Mach-Zehnder interferometer. The light in the first beam is frequency shifted by an acousto-optic deflector, which is driven by a phase-engineered radiofrequency comb designed to minimize peak-to-average power ratio. This RF comb generates multiple deflected optical beams possessing a range of output angles and frequency shifts. The second beam is shifted in frequency using an acousto-optic frequency shifter. After combining at a second beam splitter, the two beams are focused to a line on the sample using a conventional laser scanning microscope lens system. The acousto-optic deflectors frequency-encode the simultaneous excitation of an entire row of pixels, which enables detection and de-multiplexing of fluorescence images using a single photomultiplier tube and digital phase-coherent signal recovery techniques.

15 Claims, 6 Drawing Sheets

(56) References Cited

U.S. PATENT DOCUMENTS

| | | |
|---|---|---|
| 6,271,924 B1 | 8/2001 | Ngoi et al. |
| 6,297,884 B1 | 10/2001 | Drabarek |
| 6,396,069 B1 | 5/2002 | MacPherson |
| 2005/0081245 A1* | 4/2005 | Arad ............... H04N 21/4122 725/100 |
| 2000/8012929 | 6/2008 | Vaughan |
| 2008/0285606 A1* | 11/2008 | Kippenberg ............ G02F 1/39 372/32 |
| 2009/0237289 A1* | 9/2009 | Stoddard ................ H04K 3/28 342/14 |
| 2010/0210952 A1* | 8/2010 | Taira ..................... A61B 1/043 600/476 |
| 2011/0317910 A1* | 12/2011 | Suzuki ............... G02B 21/367 382/154 |

* cited by examiner

APPARATUS AND METHODS FOR FLUORESCENCE IMAGING USING RADIOFREQUENCY-MULTIPLEXED EXCITATION

CROSS-REFERENCE TO RELATED APPLICATIONS

This application is a 35 U.S.C. §111(a) continuation of PCT international application number PCT/US2014/010928 filed on Jan. 9, 2014, incorporated herein by reference in its entirety, which claims priority to, and the benefit of, U.S. provisional patent application Ser. No. 61/750,599 filed on Jan. 9, 2013, incorporated herein by reference in its entirety. Priority is claimed to each of the foregoing applications.

The above-referenced PCT international application was published as PCT International Publication No. WO 2014/110290 on Jul. 17, 2014, which publication is incorporated herein by reference in its entirety.

STATEMENT REGARDING FEDERALLY SPONSORED RESEARCH OR DEVELOPMENT

This invention was made with Government Support under: W81XWH-10-1-0518, awarded by the U.S. Army, Medical Research and Materiel Command. The Government has certain rights in the invention.

INCORPORATION-BY-REFERENCE OF MATERIAL SUBMITTED IN A COMPUTER PROGRAM APPENDIX

Not Applicable

BACKGROUND OF THE INVENTION

1. Field of the Invention

This invention pertains generally to optical imaging devices and methods and more particularly to apparatus and methods for high-speed, one and two-dimensional fluorescence imaging enabled by beat frequency multiplexing.

2. Description of Related Art

Fluorescence microscopy is one of the most important, pervasive and powerful imaging modalities in biomedical research. The spatial resolution of modern fluorescence microscopy has been improved to such a point that even sub-diffraction limited resolution is routinely possible. However, time resolution in fluorescence microscopy has not kept pace with advances in spatial resolution.

While a number of fluorescence microscopy modalities exist, the time resolution of the technique is fundamentally limited by the relatively weak optical emission of fluorescent samples. As a result, the maximum full-frame (512×512 pixels) rate of traditional single-point laser scanning fluorescence microscopy is limited to approximately a video rate of 30 frames per second, which corresponds to pixel rates of less than 10 MHz. Linescan and spinning disk confocal microscopes are capable of higher frame rates by multiplexing the fluorescence excitation and detection, but the frame rates are ultimately limited by the low electronic gain and both the optical throughput of the spinning disk and read-out time of the detector, respectively.

The demand for sub-millisecond time resolution in fluorescence microscopy has been the primary driving force behind the development of many advanced imaging technologies, such as the electron multiplier charge coupled device (EMCCD) camera, the scientific complementary metal-oxide-semiconductor (sCMOS) camera, the Nipkow spinning disk confocal microscope, and the linescan confocal microscope. While each of these devices present distinct advantages and tradeoffs between sensitivity, speed, resolution, and confocality, a device for imaging the sub-millisecond biochemical dynamics in live cells and in vivo remains an outstanding technical challenge.

High throughput imaging flow cytometry is another application in which high speed fluorescence imaging is required. Imaging of individual cells in a fluid flow, compared with measuring only scattering and single point fluorescence amplitudes, provides information that can be utilized for high-throughput rare cell detection, as well as morphology, translocation, and cell signaling analysis of a large number of cells in a short period of time. The high flow rates associated with flow cytometry demand high sensitivity photodetection and fast camera shutter speeds to generate high SNR images without blurring.

Conventional imaging flow cytometers use time delay and integration CCD techniques in order to circumvent this issue, but the serial readout strategy of this approach limits the device to a throughput of 5,000 cells per second. At this rate, high efficacy detection of rare cells using flow cytometry, such as circulating tumor cells in blood, is not practical for clinical applications.

The tradeoff between speed and sensitivity is a significant limiting factor in high-speed fluorescence microscopy systems. The ability to generate a high signal to noise ratio (SNR) image from the small number of photons emitted from a fluorescent sample during a short (sub-millisecond) time period traditionally relies on the ability of the photodetection device to provide electronic gain such that the detected signal is amplified above its thermal noise level. For this reason, high gain photomultiplier tubes (PMT) and EMCCDs are used most frequently for high-speed fluorescence imaging applications. While modern EMCCDs exhibit high quantum efficiency and gain, the gain register and pixel readout strategy is serial, which limits its overall full frame rate to fewer than 100 frames per second. PMT's offer higher gain, lower dark noise, and higher readout speed than EMCCDs, but are typically not manufactured in large array formats, limiting their utility to single-point-scanning applications. Due to the use of a PMT detector, laser scanning fluorescence microscopy is capable of high sensitivity at similar frame rates to EMCCDs, but the serial nature of the beam scanning ultimately limits the speed of image acquisition.

To date, these technological shortcomings have prevented full-frame fluorescence imaging analysis of sub-millisecond phenomena in biology. There is a need for an imaging device that can resolve the subtle dynamics of biochemical phenomena such as calcium and metabolic waves in live cells, action potential sequences in large groups of neurons, or calcium release correlations and signaling in cardiac myocytes.

Accordingly, there is need for an apparatus and method for fluorescence detection and imaging that is fast with sub-millisecond time resolution to capture dynamic processes in cells as well as flow imaging that can quickly perform high-throughput morphology, translocation and cell signaling analysis on large populations of cells. The present invention satisfies these needs as well as others and is an improvement in the art.

BRIEF SUMMARY OF THE INVENTION

The present invention provides a new approach to fluorescence stimulation, detection and imaging using radiofrequency-multiplexed excitation (FIRE) laser scanning microscopy. The FIRE system employs orthogonal frequency-domain multiplexing techniques to provide both parallel pixel excitation and nominal pixel readout rates of approximately 80 MHz. However, pixel frequencies in the range of 0.1-1,000 MHz are possible.

Acousto-optic deflectors are used to frequency-encode the simultaneous excitation of an entire row of pixels, which enables detection and de-multiplexing of fluorescence images using a single photomultiplier tube and digital phase-coherent signal recovery techniques.

Specifically, FIRE microscopy uses radiofrequency-to-space mapping to encode the excitation of a fluorescent sample into the frequency domain, such that the image can be detected using a single PMT, and demodulated using digital lock-in detection.

In one embodiment, the FIRE system is adapted to provide a scalable approach to high-speed imaging, in that it leverages the MHz bandwidths available to radiofrequency (RF) electronics and acousto-optic devices to enable MHz-equivalent pixel clock readout of hundreds of pixels simultaneously in a single data stream. Additionally, FIRE microscopy uses direct digital synthesis (DDS) to engineer the amplitude and phase of each individual pixel excitation frequency, which enables application of phase-coherent digital lock-in amplifier and orthogonal frequency-division multiplexing (OFDM) algorithms to the image de-multiplexing process in order to reduce image noise and pixel crosstalk. The system flexibility afforded by the use of direct digital synthesis enables full adjustment of the pixel number, readout rate, and field of view.

The apparatus is configured to produce frequency shifted light beams that can be used to interrogate multiple points on a sample simultaneously such that each individual point of the sample is at a distinct radiofrequency. To accomplish this, an excitation laser beam is first split into two arms of a Mach-Zehnder interferometer. The light in the first arm is frequency shifted by an acousto-optic deflector, which is driven by a phase-engineered radiofrequency comb that is designed to minimize the signal's peak-to-average power ratio. This RF comb generates multiple deflected optical beams possessing a range of both output angles as well as frequency shifts. The second arm of the interferometer is shifted in frequency using an acousto-optic frequency shifter to produce a local oscillator (LO) beam. A cylindrical lens may be used to match the angular divergence of the LO arm to that of the RF comb beams. After combining at a second beam splitter, the two beams are focused to a line on the sample using a conventional laser scanning microscope lens system. High-speed line scanning of the sample is accomplished using a resonant scan mirror in the transverse direction.

Fluorescent molecules in the sample function as square-law detectors, in that their excitation responds to the square of the total electric field. The resulting fluorescence is emitted at the various beats defined by the difference in frequencies of the two arms of the interferometer. The fluorescence emission thus oscillates at the excitation frequency with an appreciable modulation, given an excitation frequency that is not much greater than $1/\tau$, where $\tau$ is the fluorescence lifetime of the sample. For fluorophores with lifetimes in the single nanosecond range, the useable RF bandwidth of FIRE is approximately 1 GHz. Since acousto-optic devices are inherently resonant, the frequency shifter in the second arm of the interferometer is chosen to heterodyne the beat frequencies to baseband in order to maximize the useable bandwidth for a given fluorophore.

Fluorescence emission from the sample is preferably collected by the objective lens, and is detected by a PMT in a de-scanned confocal configuration, using a slit aperture to reject fluorescence emission from other sample planes.

As a demonstration of the technique, diffraction-limited confocal fluorescence imaging of stationary cells at a frame rate of 4.4 kHz, and fluorescence microscopy in flow at a velocity of 1 m s$^{-1}$, corresponding to a throughput of approximately 50,000 cells per second was performed.

In combination with fast fluorescent indicators and voltage-sensitive dyes, this high speed imaging modality has the potential to observe previously temporally-unresolved sub-millisecond dynamics in biology, which may lead to a more complete understanding of neural function, autoimmune diseases, cardiac arrhythmias, and other millisecond-timescale biological phenomena.

Beat frequency multiplexing is also applicable to other types of laser scanning microscopy, including two-photon excited fluorescence microscopy. Perhaps most notably, because emission from each pixel is tagged with a distinct radiofrequency, FIRE is inherently immune to pixel crosstalk arising from fluorescence emission scattering in the sample—the effect that typically limits the imaging depth in multifocal multi-photon microscopy. In combination with fast fluorophores, FIRE microscopy is capable of observing nano- to microsecond timescale phenomena using fluorescence microscopy.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes several embodiments of the system scheme of the present invention and the associated methods for fluorescence excitation and detection are depicted generally in FIG. 1 through FIG. 7. It will be appreciated that the methods may vary as to the specific steps and sequence and the apparatus architecture may vary as to structural details, without departing from the basic concepts as disclosed herein. The method steps are merely exemplary of the order that these steps may occur. The steps may occur in any order that is desired, such that it still performs the goals of the claimed invention.

Figure 1:
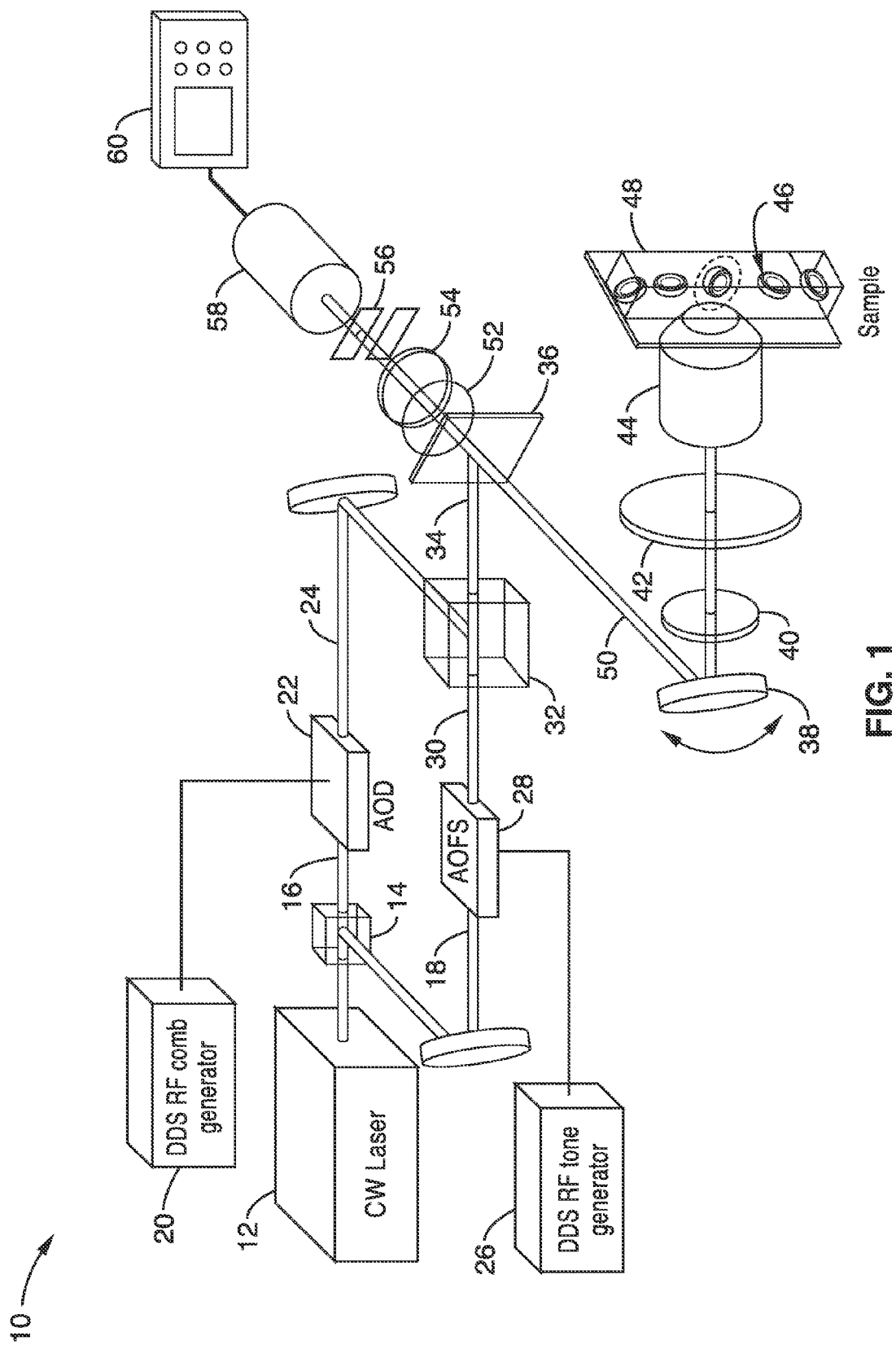
FIG. 1 is a schematic diagram of one embodiment of an apparatus for fluorescence imaging according to the invention.
Figure 2A:
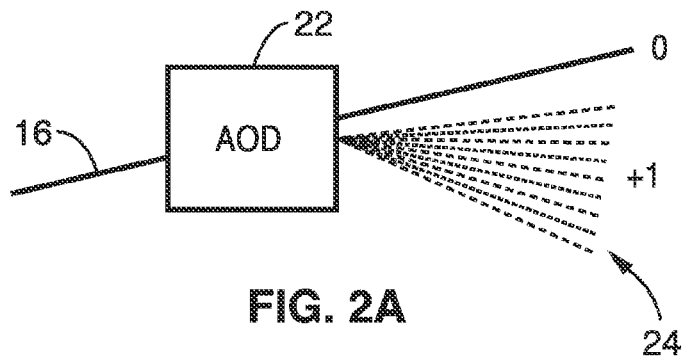
FIG. 2A is a schematic diagram of an acousto-optic deflector element of FIG. 1 that produces a single diffracted first-order beam for each radiofrequency comb frequency.
Figure 2B:
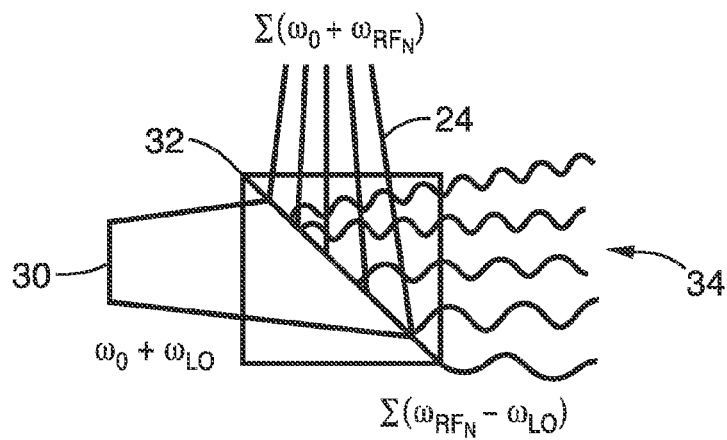
FIG. 2B is a schematic diagram of a beam splitter showing beat frequency generation from mixed frequency shifted beams.

Turning now to FIG. 1, FIG. 2A and FIG. 2B, one embodiment of an apparatus 10 for fluorescence imaging using radiofrequency multiplexed excitation is schematically shown to illustrate the invention. Exciting individual points on the sample at a distinct radiofrequency is an important feature of FIRE apparatus and procedure. In the embodiment shown in FIG. 1, beat frequency excitation multiplexing is performed by using acousto-optic devices in a Mach-Zehnder interferometer (MZI) configuration.

An excitation laser 12 produces a beam that is split by a non-polarizing beam splitter 14 and the resulting first beam 16 is directed to an acousto-optical deflector (AOD) 22 and the second beam 18 from the splitter 14 is directed to an acousto-optic frequency shifter (AOFS) 28.

As shown in FIG. 1, the excitation light beam 16 in one arm of the MZI can be frequency shifted by a 100 MHz bandwidth AOD 22, for example, driven by a comb of radiofrequencies produced by the DDS RF comb generator 20. The comb of radiofrequencies from the DDS RF comb generator 20 is preferably phase-engineered to minimize its peak-to average power ratio. As seen in FIG. 2A, the AOD 22 produces multiple deflected optical beams 24 with a range of both output angles and frequency shifts. The AOD 22 produces a single diffracted first-order beam for each radiofrequency comb frequency.

Light beam 18 in the second arm of the interferometer passes through an acousto-optic frequency shifter 28, preferably driven by a single radiofrequency tone produced by a DDS RF tone generator 26, which provides a local oscillator (LO) beam 30. A cylindrical lens (not shown) may be placed after the AOFS 28 to match the divergence of the local oscillator (LO) beam 30 to that of the radiofrequency beams.

At the MZI output, the two beams 24, 30 are combined by a second beam splitter 32. FIG. 2B also shows the beat frequency generation at the MZI output and beam splitter 32. The combined beam 34 is ultimately focused to a horizontal line on the sample, mapping frequency shift to space using a conventional laser scanning microscope lens system.

In the apparatus of FIG. 1, the combined beam 34 is reflected from dichroic mirror 36 to a resonant scan mirror galvanometer 38 to the sample through the scan lens 40, tube lens 42 and objective lens 44. The sample cells 46 are in a channel 48 and are brought through the combined beam 34 in this illustration.

Fluorescence emissions 50 from the exposed sample 46 are detected by a photomultiplier tube (PMT) 58 in a confocal configuration, using a slit aperture 56 to reject out-of plane fluorescence emission. A resonant scan mirror 38 performs high-speed scanning in the transverse direction for two-dimensional imaging. Points in the horizontal direction are excited in parallel at distinct radio frequencies. Scanning this line scan excitation in the vertical direction using a galvanometer generates a two-dimensional image.

In the embodiment of FIG. 1, the emission beam 50 from the objective lens 44, tube lens 42, scan lens 40 and resonant scanning mirror 38 is directed through the dichroic mirror 36 and fluorescence emission filters 52, 54 and slit aperture 56 to at least one photomultiplier tube 58. The photomultiplier tube 58 is coupled to a computation and recording device 60 such as a digital recording oscilloscope.

In one embodiment, the computation device 60 is configured to control the other components such as the resonance scan mirror 38, laser 12, RF comb 20 and RF tone 26 generators, and optics as well as process the PMT signals. The computation device may also have a display.

Accordingly, a method for fluorescence excitation and detection is provided utilizing frequency shifted light that can be used to interrogate multiple points on a sample simultaneously. One method 70 for fluorescence excitation and detection is shown schematically in FIG. 3. At block 72 of FIG. 3, frequency shifted beams of light are created. Frequency shifted beams of light can be created by different methods. A single diffracted first order beam for each radio frequency comb frequency can be produced with an acousto-optic deflector as shown in FIG. 2A.

Because fluorescent molecules in the sample 46 function as square-law detectors of the total optical field, fluorescence is excited at the various beats defined by the difference in frequencies of the two arms of the interferometer. Given the finite frequency response of fluorophores, the LO beam frequency shift is chosen to heterodyne the beat frequency excitation spectrum to the baseband to maximize the usable modulation bandwidth. This is necessary because AODs typically operate over an upshifted, sub-octave passband to avoid harmonic interference.

Direct digital synthesis (DDS) of the radiofrequency comb 20 used to drive the AOD 22 defines each pixel's excitation by a specific radiofrequency and phase, resulting in phase coherence between the radiofrequency comb and the detected signal. This phase coherence enables image de-multiplexing using a parallel array of phase-sensitive digital lock-in amplifiers, implemented in the computer 60. FIRE's parallel readout results in a maximum pixel rate equal to the bandwidth of the AOD.

Since each pixel's excitation is defined by a specific radiofrequency and phase using the direct digital synthesizer (DDS), the detected fluorescence is phase-shifted and scaled with respect to the driving signal. This phase-coherent emission enables digital lock-in amplifier signal recovery, a well known ultra-sensitive detection technique.

Figure 3:
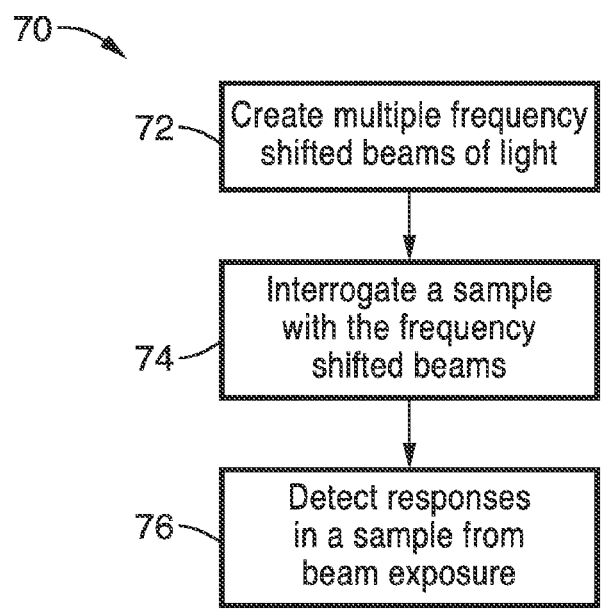
FIG. 3 is a flow diagram of one method for inducing and detecting fluorescence from a sample with frequency shifted beams according to the invention.

At block 74 of FIG. 3, a sample is interrogated with the frequency shifted beams with each point at a distinct radio frequency to excite fluorescence in the sample. The response of the sample to exposure to the frequency shifted beams is detected at block 76 of FIG. 3.

A significant feature of the FIRE apparatus and methods is its ability to excite fluorescence in each individual point of the sample at a distinct radiofrequency. Digitally synthesized radiofrequency "tagging" of the fluorescence emission of each pixel occurs at the beat frequency between two interfering frequency-shifted laser beams. With frequency domain multiplexing, each pixel in a row of a FIRE image is assigned its own radiofrequency. In a two-dimensional FIRE image, pixels are analogous to points on a time-frequency Gabor lattice. A single-element photodetector simultaneously detects fluorescence from multiple pixels, and an image is reconstructed from the frequency components of the detector output, which are resolved using parallel lock-in amplification in the digital domain. The response of the sample to exposure to the frequency shifted beams is detected at block 76 of FIG. 3. The analysis of the detected signal may be simply a multi-point measurement of the sample or may include the creation of an image of the subject.

Figure 4:
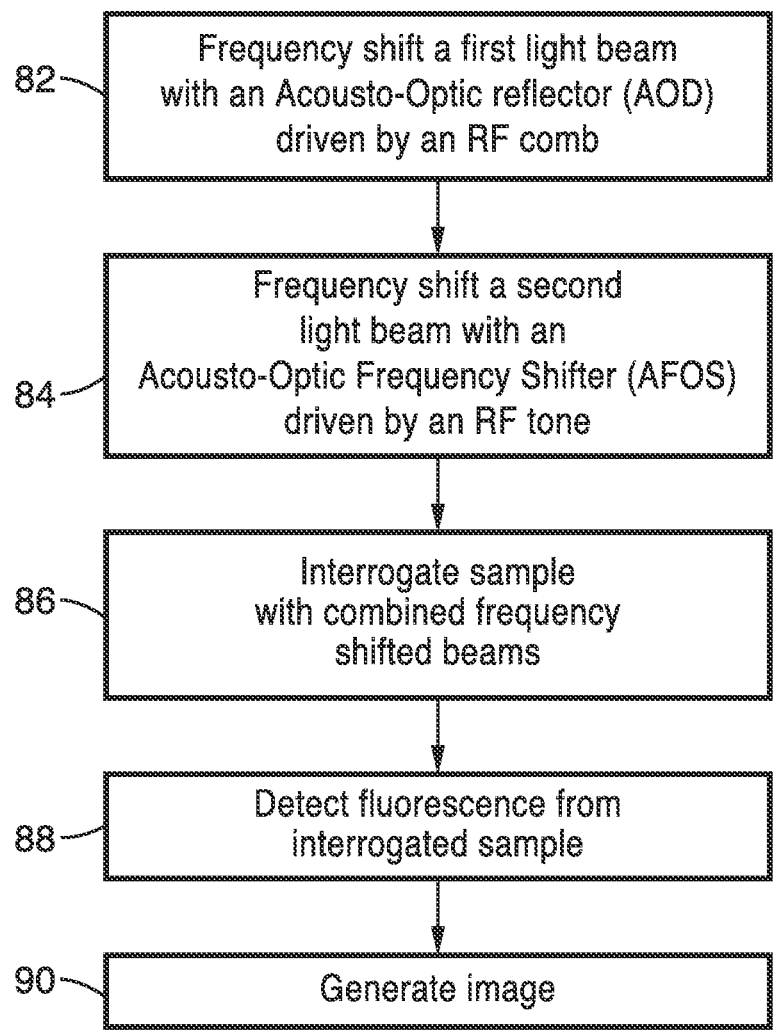
FIG. 4 is a flow diagram of one method for fluorescence microscopy according to the invention.

One adaptation of the method for fluorescence microscopy 80 is shown schematically in FIG. 4. At block 82, a frequency shift of a first light beam is performed with an acousto-optic deflector driven by a comb of radiofrequencies, preferably phase-engineered to minimize its peak to average power ratio. The acousto-optic deflector (AOD) produces multiple deflected optical beams with a range of both output angles and frequency shifts.

Light from a second beam passes through an acousto-optic frequency shifter, driven by a single radiofrequency tone, which provides a local oscillator (LO) beam at block 84 of FIG. 4. An optional cylindrical lens may be used to match the LO beam's angular divergence to that of the radiofrequency comb beams.

Interrogation of the sample with the beams at block 86 preferably uses a pixel multiplexing approach using beat frequency modulation. In one embodiment, the frequency shifted beams are directed to a sample using a conventional line scanning microscope lens system. High-speed line scanning of the sample can be accomplished using a resonant scan mirror in the transverse direction.

Since the excitation of the fluorescent molecules in the sample responds to the square of the total electric field, the resulting fluorescence is emitted at the various beats defined by the difference frequencies of the first and second interrogating beams:

$$E_t = E_{RF} + E_{LO}$$

$$|E_t|^2 = E_t^* E_t = 2E_0^2\{1 + \cos(\omega_{RF} t)\}$$

Interference of two frequency shifted waves results in amplitude modulation of the resulting intensity at the beat frequency:

$$E_{RF} = E_0 e^{j(\omega_0 + \omega_{RF})t}$$

$$E_{LO} = E_0 e^{j\omega_0 t}$$

The fluorescence emission thus oscillates at the excitation frequency with an appreciable modulation, given an excitation frequency not much greater than $1/\tau$, where $\tau$ is the fluorescence lifetime of the sample.

The maximum modulation frequency, and thus maximum pixel readout rate, is intrinsically limited by the sample's fluorescence lifetime. If the excitation frequency is less than $1/\tau$, where $\tau$ is the fluorescence lifetime of the sample, the emitted fluorescence will oscillate at the excitation frequency with appreciable modulation.

Furthermore, beat-frequency modulation is fundamental to the speed of FIRE; the beating of two coherent, frequency-shifted optical waves produces a single radiofrequency tone, without any harmonics that can introduce pixel crosstalk and reduce the usable bandwidth. Because the FIRE system is designed so that every pixel is spatially resolved at the diffraction limit, beating of the excitation light from two adjacent pixels generates a fluorescence signal at the comb spacing frequency.

However, this frequency lies out of the image band and does not produce pixel crosstalk. With respect to blur-free imaging of fast phenomena in samples such as living cells, the speed of the fastest dynamic event that can be imaged is determined by the maximum allowable sideband frequency (half the comb spacing).

The spatial resolution, number of pixels and field of view can also be designed. The FIRE microscope is a diffraction-limited technique. Like other laser scanning microscopy techniques, the minimum transverse spatial resolution is the diffraction limited spot size determined by the numerical aperture of the objective and the laser excitation wavelength.

The preferred pixel rate of the system is equal to the product of the nominal line rate and the number of pixels per line. With the nominal line rate limited to the comb spacing, the maximum pixel rate of FIRE is equal to the bandwidth of the AOD ($B_{AOD}$), given $B_{AOD} = p_x \times r_{line}$, where $p_x$ is the number of pixels in a line, and $r_{line}$ is the line rate. The x-axis was chosen as the AOD deflection direction.

The number of resolvable points per line is equal to the time-bandwidth product of the AOD ($TBP_{AOD}$). To satisfy the Nyquist spatial sampling criterion, the number of pixels per line should be at least twice this value, $P_x = 2 \times TBP_{AOD}$.

The field of view in the x-direction ($FOV_x$) is the number of resolvable points times the diffraction-limited spot-size, d: given $FOV_x = d \times TBP_{AOD} = d \times p_x/2$.

Nyquist oversampling in the y-direction should also be satisfied. In the case of 2-D imaging with a scan mirror, the frame-rate, field of view and number of pixels in the y-direction should satisfy the relations $p_y \times r_{frame} = r_{line}$ and $FOV_y = d \times p_y/2$, where $r_{frame}$ is the 2-D frame rate. The range of the scan mirror should be chosen to match the $FOV_y$ above.

These criteria for oversampling in the y-direction are not unique to FIRE, and can be satisfied for any imaging system. However, satisfying the Nyquist criterion in the y-direction is particularly preferred for FIRE. Under-sampling in the y-direction can lead to a rate of change of fluorescence that is greater than half the line-rate, even for static samples. In the frequency domain, the generated sidebands will extend beyond half the frequency comb spacing, resulting in inter-pixel cross talk and blurring in the x-direction.

With oversampling of each diffraction limited spot of a sample, this blurring effect can be avoided. For dynamic samples, such as live cells, the frame rate and pixel frequency spacing should also be chosen appropriately to avoid side-band blurring, depending on the sample dynamics. The pixel spacing in frequency space must be at least twice as large as the maximum rate of change of the fluorescence signal. The optical system magnification should be adjusted such that individual pixels are spatially resolved at the sample.

In the FIRE system described above, the fastest line scan shutter speed is 1.25 ms (800 kHz comb spacing), which allows for the capture of pixel dynamics with frequency content up to 400 kHz.

Fluorescence from the interrogated sample is detected over time at block 88 and an image can be generated at block 90 of FIG. 4. Detection is preferably performed by at least one photomultiplier tube (PMT). However, other detection schemes may be adapted.

Fluorescence imaging generates darkfield images of samples by estimating the number of emitted photons from each excited pixel of a sample. In conventional fluorescence imaging, the number of photons is estimated through integration of the optical signal. In FIRE, the light emitted from each pixel is modulated at a particular radiofrequency, and the strength of the signal coming from each pixel is differentiated either by performing a short time Fourier transform, or demodulating the signal from each pixel using parallel digital lock-in amplification, for example. As a result, FIRE reads out multiple pixels in parallel, increasing imaging speed and increasing the integration time for a given frame rate.

The flexibility afforded by digitally synthesizing the amplitude and phase of the radiofrequency spectrum provides complete, real-time control over the number of pixels, pixel frequency spacing, pixel non-uniformity and field of view. Because PMTs inherently have a smaller dynamic range than CCD or CMOS technologies, maximizing this quantity per pixel is important to the performance of the FIRE procedure. Specifically, phase-engineering the excitation frequency comb enables the dynamic range of each pixel to scale as $D/\sqrt{M}$, where D is the dynamic range of the PMT, and M is the pixel-multiplexing factor. This is in contrast to the case where the initial phases of all of the excitation frequencies are locked, which yields images with a dynamic range of D/M.

Although FIRE fundamentally presents a tradeoff in dynamic range for speed, it improves in sensitivity when compared to single point scanning fluorescence microscopy, as multiplexing the sample excitation by a factor of M yields an M-fold increase in the dwell time of each pixel. However, due to the parallel nature of detection, FIRE shares shot noise across all pixels in a row. This causes the shot noise-limited uncertainty at each pixel to scale with the square root of the total number of photons collected from all pixels in a line scan. The extent to which this effect degrades the SNR at each pixel depends inversely on the sparsity of the sample.

As described previously, direct digital synthesis of the local oscillator (LO) and radiofrequency (RF) comb beams can be accomplished using the two outputs of a 5 GS/s arbitrary waveform generator, for example, which are amplified to drive the acousto-optic deflector (AOD) and acousto-optic frequency shifter (AOFS). After photodetection and digitization, two digital de-multiplexing algorithms can be used to recover the fluorescence image from the frequency multiplexed data. The first method to recover the fluorescent signal employs a short time Fourier transform (STFT). The second method uses an array of digital lock-in amplifiers to heterodyne and de-multiplex each comb-line separately.

Figure 5:
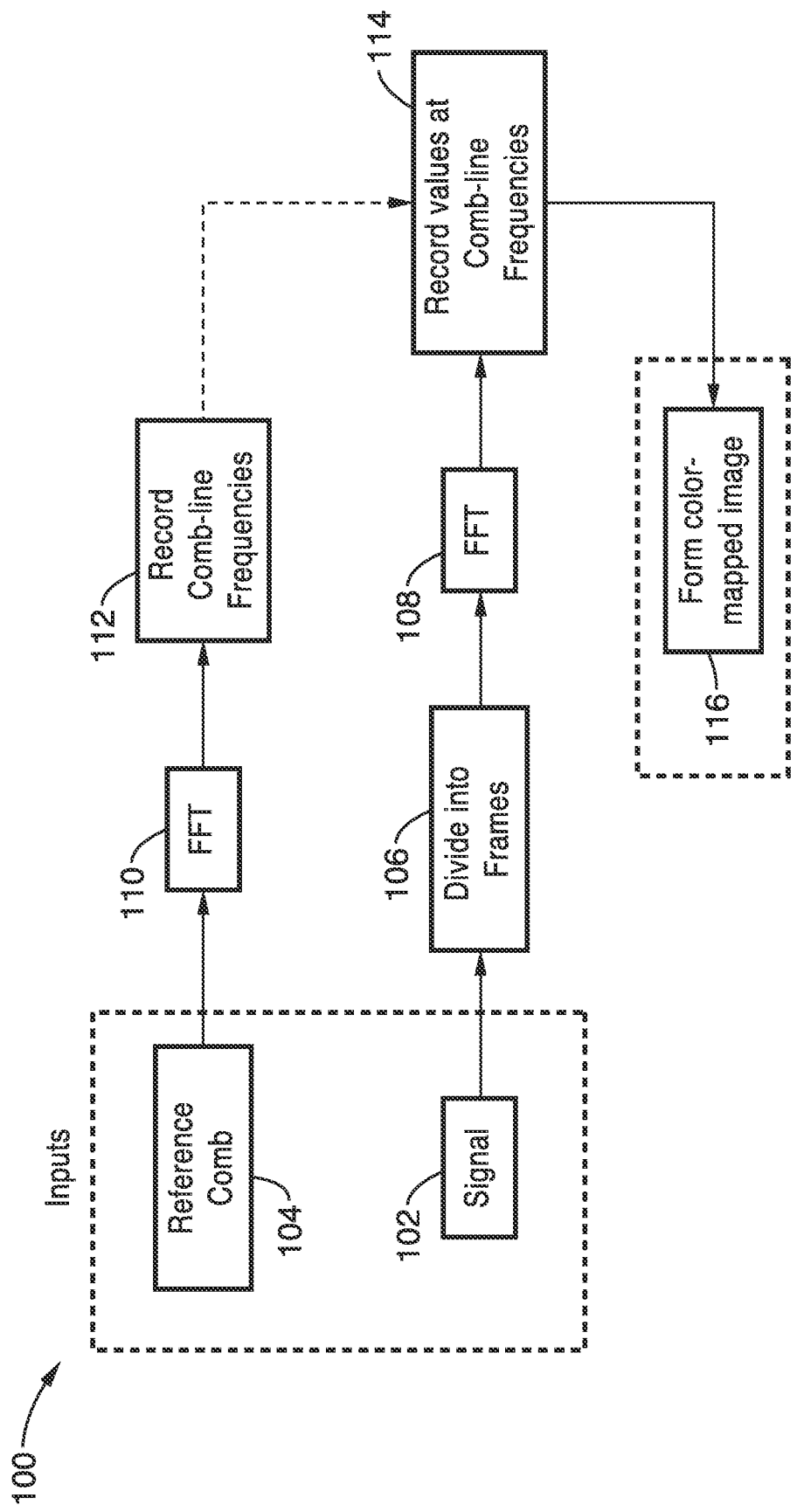
FIG. 5 is a flow diagram of one image reconstruction algorithm according to the invention.

The image reconstruction algorithm 100 of the first method is shown schematically in FIG. 5. The STFT method works by segmenting the data sequence into frames, and performing a discrete Fourier transform (DFT) on each frame to recover the frequency-multiplexed signal. Each frame corresponds to a 1D line-scan. In order to avoid pixel-pixel cross talk from power spreading across frequency bins, the time duration of each frame is set as an integer multiple of the inverse of the frequency comb spacing. In this case, the frequency channels are said to be orthogonal, and the DFT bins lie precisely on the frequency comb lines. The maximum line rate in this scenario is equal to the frequency comb spacing and corresponds to 300 kHz, 400 kHz, and 800 kHz line rates.

Accordingly, as seen in FIG. 5, the signal input 102 is divided into frames 106 and subject to a fast Fourier transform 108. At the same time, the reference comb 104 is subject to a fast Fourier transform 110 and the comb-line frequencies are identified and recorded at 112. The signal values at the comb-line frequencies are recorded at block 114 and a color-mapped image is then generated 116.

Figure 6:
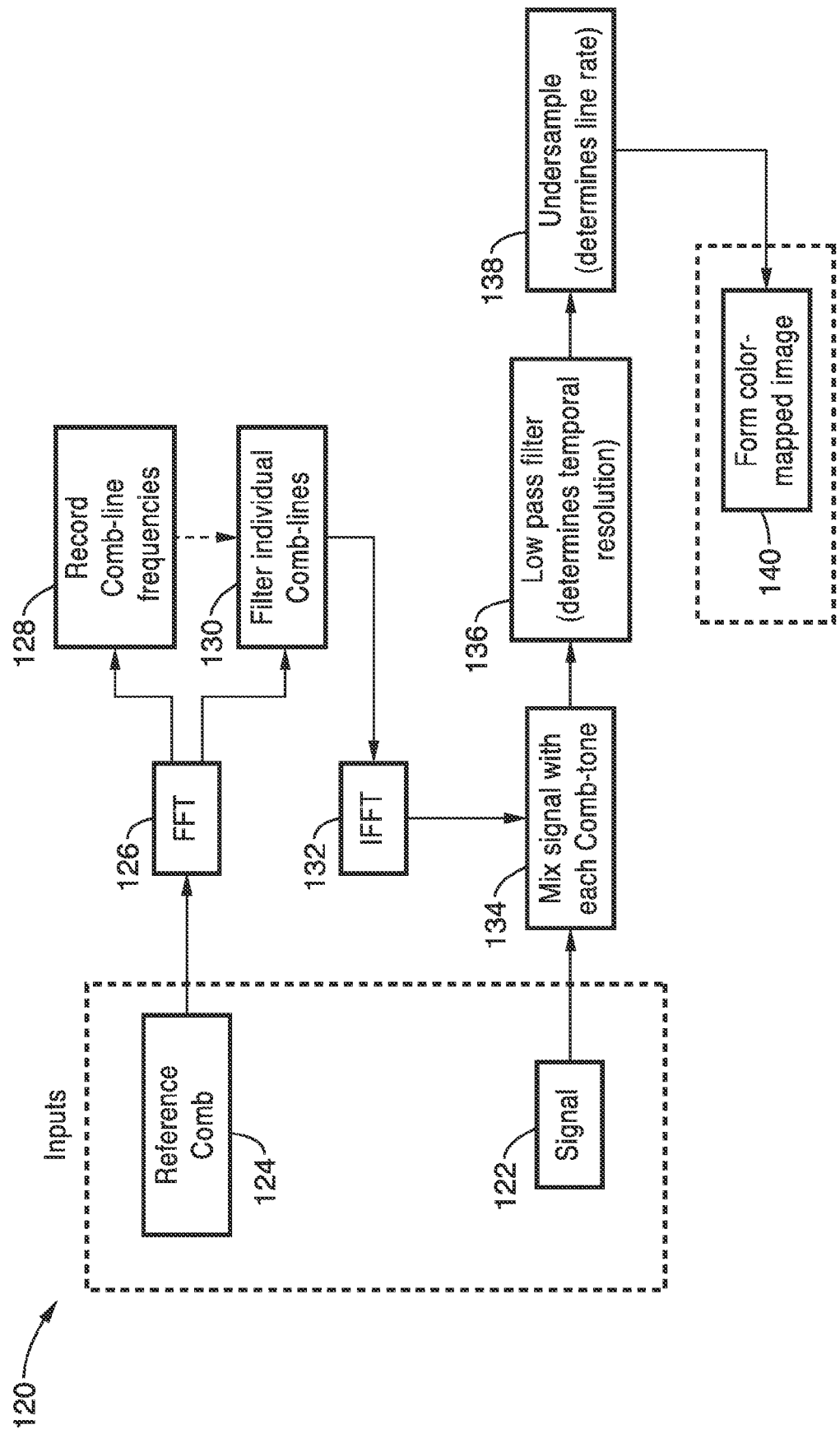
FIG. 6 is a flow diagram of a second image reconstruction algorithm according to the invention.
Figure 7:
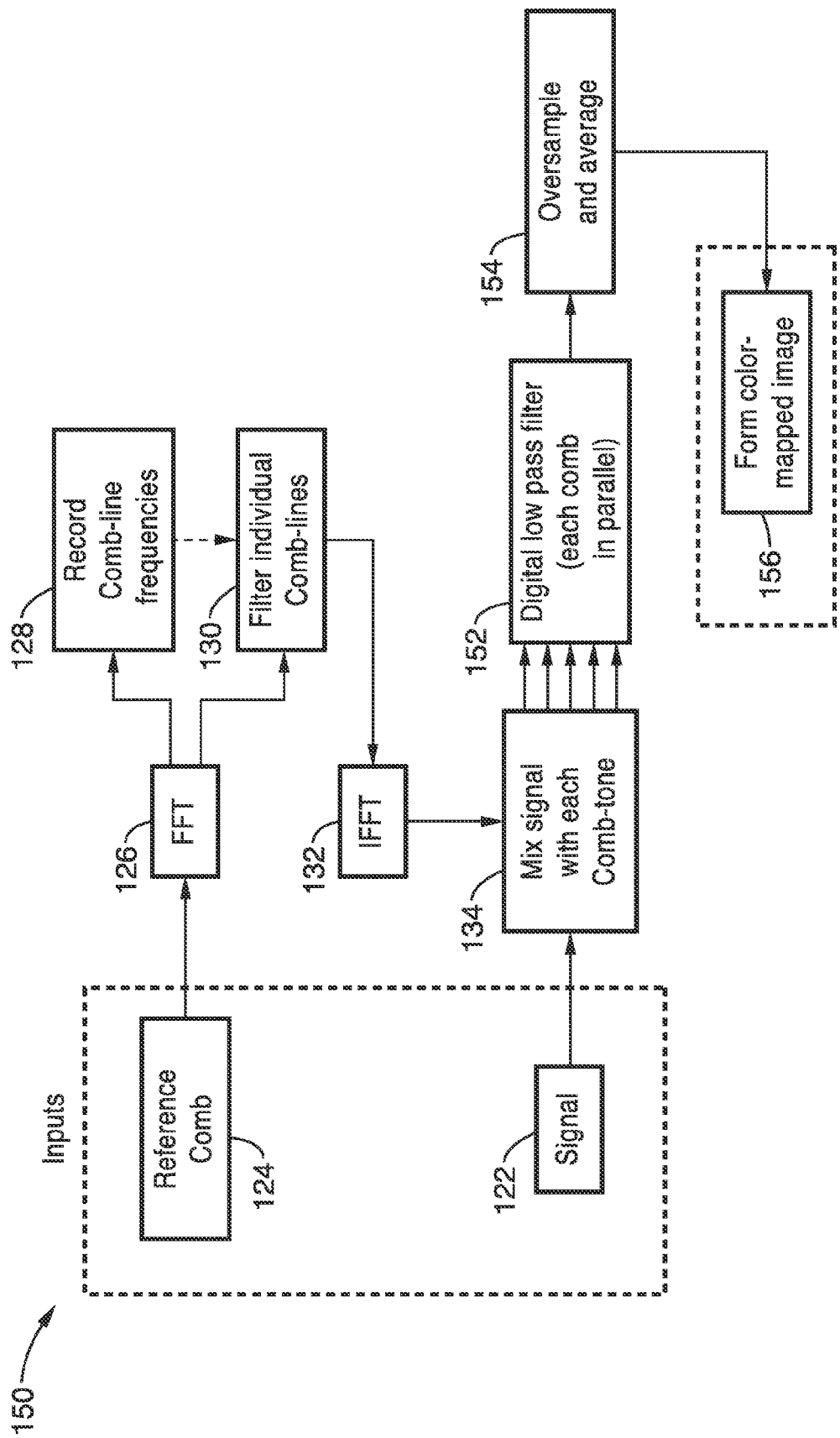
FIG. 7 is a flow diagram of a third image reconstruction algorithm according to the invention.

In the second image reconstruction method, there are two digital lock-in amplifier approaches that may be used that are illustrated in FIG. 6 and FIG. 7 respectively. Generally, in the second image reconstruction, a lock-in amplifier demodulation technique is implemented by digitally mixing the data signal with copies of each frequency comb line. The mixing of the comb lines and the signal downshifts the corresponding comb line to baseband. A low pass filter (LPF) can be used to extinguish all other comb lines, leaving only the modulated fluorescent signal from the comb line of interest. To obviate phase locking the reference to the signal, both in-phase (I) and quadrature phase (Q) mixing terms may be calculated. The magnitude of the sum of I- and Q-channels is equal to the amplitude of the signal. The bandwidth of the LPF is less than half the comb spacing to prevent pixel crosstalk in frequency space. With the reduced analog bandwidth after filtering, each pixel's signal can be boxcar-averaged and under-sampled to at least the Nyquist rate, equal to the frequency comb spacing. The under-sampled data rate corresponds to the line rate of the system.

Accordingly, the image reconstruction 120 in FIG. 6, the signal 122 and reference comb 124 are provided as inputs. The reference comb 124 is subject to a fast Fourier transform 126 and the comb-line frequencies are recorded at 128 and the individual comb-lines are filtered at 130. The filtered comb-lines 130 are subject to an inverse fast Fourier transform 132 and the signal 122 is mixed with each comb-tone at 134. The mixed signal is filtered with a low pass filter 136 to determine the temporal resolution that is undersampled at 138 to determine the line rate. A color mapped image is then formed 140 from the resulting signal.

An alternative embodiment of the lock-in amplifier demodulation image reconstruction is shown in FIG. 7. Here, the same reference comb processing and initial signal processing takes place as shown in FIG. 6. However, each comb of the mixed signal/comb-tone output is filtered in parallel by a digital low pass filter 152. The filtered signal is oversampled and averaged at block 154 and a color-mapped image is formed at block 156.

Although both the DFT and lock-in techniques can be used to de-multiplex the fluorescence image, the lock-in technique has certain advantages: (a) there is no orthogonality requirement, leaving more flexibility in comb line configuration, (b) the nominal line rate is determined by the under-sampling factor, allowing for line-rates above the minimum Nyquist rate, and (c) the reference and signal can be phase locked, either by a priori estimation of the signal phase or via deduction from the ratio of I and Q channels. Phase locked operation rejects out of phase noise, resulting in a 3-dB improvement in the signal to noise ratio (SNR).

The invention may be better understood with reference to the accompanying examples, which are intended for purposes of illustration only and should not be construed as in any sense limiting the scope of the present invention as defined in the claims appended hereto.

Example 1

In order demonstrate the operational principles of FIRE microscopy, a sample of immobilized 15-µm diameter fluorescent polystyrene beads were imaged using 256 excitation frequencies spaced by 300 kHz (total bandwidth of 76.8 MHz). The images were collected at a frame rate of 4.2 kHz. The detected time-domain PMT signal offers no indication of the lateral bead location. A fast Fourier transform (FFT) of three windows of the signal was used to indicate the different frequency components associated with the positions of each bead.

This illustrated the frequency-to-space mapping of the sample excitation and emission. The vertical location of the beads in the image was recovered from the reference output of the resonant scan mirror. To avoid nonlinear space-to-time mapping from the resonant scan mirror in the vertical direction, an aperture is placed in the intermediate image plane to limit the sample excitation to the linear portion of the scan field, and a sine correction algorithm is further applied to the image to compensate for any residual distortion in the image.

The axial resolution of the FIRE system was measured by exciting a 500 nm fluorescent bead with 488-nm excitation, and scanning the sample through the focus at 1 µm intervals, using 488-nm excitation. A 100×, 1.4-NA oil immersion objective was used in combination with a 200-mm focal length tube lens and a 100-µm tall slit aperture placed before the PMT. A Gaussian fit to the data showed a 5.9 µm FWHM. This axial resolution could be further improved through the use of a smaller slit, as the 100 µm slit is larger than the Airy disk at this magnification.

To demonstrate the ability of two-dimensional FIRE to record fluorescent dynamic phenomena, fluorescent beads flowing at a velocity of 2.3 mm s$^{-1}$ inside a microfluidic channel were imaged. In the two-dimensional implementation of FIRE, images are acquired on an inverted microscope, in a de-scanned configuration, using a 2.2 kHz resonant scan mirror. To avoid nonlinear space-to-time mapping from the resonant scanner in the vertical direction, an aperture was placed in the intermediate image plane of the imaging system to limit the sample excitation to the approximately linear portion of the scan field. A sine correction algorithm was further applied to the image in Matlab to compensate for any residual distortion in the image arising from the sinusoidal deflection pattern of the mirror. Brightness and contrast adjustments, thresholding, and 2-dimensional low-pass filtering were performed on all images.

Fluorescence emission was detected by a bialkali photo-multiplier tube (PMT) (R3896, Hamamatsu) after passing through a dichroic mirror and a bandpass filter. The current signal from the PMT was amplified by a 400-MHz bandwidth current amplifier with 5 kV/A transimpedance gain. This voltage signal was digitized using a 250 MS/s, 8-bit resolution oscilloscope. For 2-D scanned images, the reference output from the resonant scan mirror was used for triggering, and was also digitized and saved for image reconstruction. For the flow cytometry experiments, the digitizer was triggered off of the image signal itself. The digitized data was then transferred to a PC for signal processing.

Example 2

To demonstrate FIRE microscopy on biological samples, adherent cells stained with various fluorophores were imaged at a frame rate of 4.4 kHz. NIH 3T3 mouse embryonic fibroblasts, C6 astrocyte rat glial fibroblasts and *Saccharomyces cerevisiae* yeast were stained with a fluorescent cytosol stain (Calcein AM) or nucleic acid stain (Syto16). NIH 3T3 and MCF-7 cells and C6 astrocytes were propagated in Dulbecco's Modified Eagle Medium with 10% fetal bovine serum and 1% penicillin streptomycin at 37° C. and 5% $CO_2$. Liquid cultures of *Saccharomyces cerevisiae* were grown in tryptic soy broth at 240 rpm and 37° C.

Prior to staining, cultured mammalian cells were released from culture flasks, seeded on glass slides, and allowed to spread for 24 hours. Mammalian cells were stained with either 4 µM Syto16 green fluorescent nucleic acid stain in phosphate buffered saline (PBS) for 30 minutes, 1 µM Calcein Red-Orange AM in culture media for 45 minutes, or 1 µM Calcein AM in culture media for 45 minutes. Cells were washed twice with PBS then fixed for 10 minutes with 4% paraformaldehyde in PBS. Following fixation, cells were washed twice with PBS and prepared for either stationary or flow-through microfluidic imaging.

For stationary imaging, number 1.5 cover glasses were placed on slides and sealed. In an effort to preserve the shape of adhered mammalian cells for flow-through microfluidic experiments a cell scraper was used to remove and spread the stained and fixed cells from glass slides. The cells were diluted in PBS.

*S. cerevisiae* were stained in suspension using the same concentration of Calcein AM for 45 minutes, washed twice with PBS, fixed with 4% paraformaldehyde in PBS, and washed twice with PBS. For stationary imaging, the cells were seeded on glass slides and sealed under number 1.5 coverslips.

To compare FIRE microscopy with wide-field fluorescence imaging, laser excitation at 488 nm was used for FIRE imaging (8.5 mW per pixel, measured before the objective), and mercury lamp excitation was used for wide-field imaging. All FIRE images that were generated used a radiofrequency comb frequency spacing of 400 kHz, and were composed of 200×92 pixels. Slight vignetting was observed in the FIRE images due to the mismatch of the Gaussian profile of the LO beam with the flat-top radiofrequency comb beam. This mismatch and the resulting vignetting can be eliminated using digital pre-equalization of the radiofrequency comb in the direct digital synthesis generator.

Images of cells were taken with both the FIRE microscope and a conventional widefield fluorescence microscope based on a 1,280×1,024 pixel CMOS camera. The frame rate difference of nearly three orders of magnitude is mitigated by the gain of the PMT detector combined with digital lock-in amplifier image demodulation. Comparisons of single frames indicated that the intensity per pixel of the FIRE excitation was approximately 10 times that of the wide-field excitation. However, the total excitation energy incident upon the sample per pixel per frame in the FIRE images was 100 times less than in the wide-field images.

Example 3

Flow cytometry is an application that requires high-speed fluorescence measurements. Compared to single-point flow cytometry, imaging flow cytometry provides information that can be particularly useful for high-throughput rare cell detection. The high flow velocities associated with flow cytometry demand fast imaging shutter speeds and high-sensitivity photodetection to generate high-SNR, blur-free images. Conventional imaging flow cytometers use time delay and integration CCD technology to circumvent this issue, but the serial pixel readout strategy of this technology currently limits devices to a throughput of approximately 5,000 cells per second.

To demonstrate high-speed imaging flow cytometry using FIRE, a single stationary line scan of 125 pixels spaced by 800 kHz (pixel readout rate of 100 MHz, line scan rate of 800 kHz) was used to image Syto16-stained MCF-7 human breast carcinoma cells flowing in a microfluidic channel at a velocity of 1 m s$^{-1}$. Assuming a cell diameter of 20 mm, this velocity corresponds to a throughput of 50,000 cells per second.

For the imaging flow cytometry, MCF-7 breast carcinoma cells were stained with Syto16, prior to fixation with formaldehyde. The cells were then suspended in phosphate-buffered saline, and flowed through a linear, rectangular cross-section 110 µm×60 µm microfluidic channel made from polydimethylsiloxane, using a syringe pump, at a fixed volumetric rate. The fluid flow velocity is calculated using the equation V=Q/A where Q is the volumetric flow rate, and A is the cross-sectional area of the channel. Vertical scaling calibration of the images was performed after imaging 10 µm spherical beads flowing at the same volumetric flow rate.

For comparison, Syto16-stained MCF-7 cells in a fluid flow at the same velocity using a frame transfer EMCCD in single exposure mode (512×512 pixels) were also imaged. Although the high sensitivity and gain of the EMCCD together yield a reasonable SNR image, the camera's minimum exposure time of 10 ms and its frame transfer nature create significant blur at these flow velocities. In contrast, the FIRE line scan shutter speed of 1.25 ms yields blur-free images with comparable SNR. This configuration of the FIRE system features pixel readout rates in the 100 MHz range, but this rate can be directly extended to more than 1 GHz through the use of wider bandwidth acousto-optic deflectors. FIRE's maximum modulation frequency, and thus maximum pixel readout rate, is intrinsically limited by the sample's fluorescence lifetime.

It can be seen that the radiofrequency-multiplexed excitation approach of the method can be adapted to many different diagnostic devices. For example, the methods can be adapted to Fast laser scanning fluorescence microscopy used in neurology, physiology, immunology, research. The method can be adapted for use in multi-photon excited fluorescence microscopy as well as stimulated Raman, CARS, 2nd harmonic and 3rd harmonic microscopy, etc. Other imaging modalities such as fast fluorescence lifetime imaging microscopy (frequency domain FLIM), imaging flow cytometry using fluorescence and multi-flow channel simultaneous single-point fluorescence-based flow cytometry can also benefit from the methods.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An apparatus for optical interrogation of a sample, comprising (a) a first beam generator, comprising (1) a laser light source; (2) an acousto-optic deflector; and (3) a radio frequency comb generator; (b) a second beam generator, comprising: (1) a laser light source; (2) an acousto-optic frequency shifter; and (3) a radio frequency tone generator; (c) an objective lens system configured to expose a sample to beams from the first and second beam generators over time; and (d) a photodetector; wherein light emissions from the sample from exposure to beams from the first and second beam generators are detected by the photodetector.

2. An apparatus as recited in any previous embodiment, wherein the objective lens system comprises: a scanning mirror; a scan lens; a tube lens; and an objective lens.

3. An apparatus as recited in any previous embodiment, wherein the photodetector comprises: a fluorescence emission filter; a slit aperture; and a photo-multiplier tube.

4. An apparatus as recited in any previous embodiment, the photodetector further comprising: a computer with programming for generating an image of the sample from detected fluorescence emissions.

5. An apparatus as recited in any previous embodiment, further comprising: a non-polarizing beam splitter configured to combine a beam from the first beam generator with a beam from the second beam generator to produce a combined beam that is directed through the objective lens system to a sample.

6. An apparatus as recited in any previous embodiment, wherein the RF comb generator comprises a direct digital synthesizer (DDS) RF comb generator and said RF tone generator comprises a direct digital synthesizer (DDS) RF tone generator.

7. An apparatus as recited in any previous embodiment, further comprising: a controller configured to control the objective lens system and the photodetector.

8. An apparatus for fluorescence imaging, comprising: (a) a laser excitation source; (b) an acousto-optic interferometer for splitting light from the laser excitation source into first and second frequency shifted beams; (c) a beam splitter and lens system for combining the frequency shifted beams and focusing the combined beams on a sample; (d) a photodetector for simultaneously detecting fluorescence emissions from all points on the sample; and (e) a computer coupled to the photodetector with programming for generating an image of the sample from the detected fluorescence emissions.

9. An apparatus as recited in any previous embodiment, wherein the first frequency shifted beam of the acousto-optic interferometer is produced with a direct digital synthesizer (DDS) RF comb generator and an acousto-optic deflector.

10. An apparatus as recited in any previous embodiment, wherein the second frequency shifted beam of the acousto-optic interferometer is produced with a direct digital synthesizer (DDS) RF tone generator and an acousto-optic frequency shifter.

11. An apparatus as recited in any previous embodiment, wherein the photodetector comprises: a dichroic mirror; a fluorescence emission filter; a slit aperture; and a photo-multiplier tube.

12. A method of fluorescence imaging, the method comprising: (a) creating a first beam of frequency shifted light; (b) creating a second beam of frequency shifted light; (c) interrogating a sample with the first and second beams of light; and (d) detecting a response in the sample from exposure to the beams of frequency shifted light.

13. A method as recited in any previous embodiment, further comprising: combining the first beam and the second beam to produce a combined beam; and interrogating the sample with the combined beam.

14. A method as recited in any previous embodiment, wherein the first beam is created with an acousto-optic deflector driven by an RF comb and an excitation laser beam.

15. A method as recited in any previous embodiment, wherein the second beam is created with an acousto-optic frequency shifter driven by an RF tone and an excitation laser beam.

16. A method as recited in any previous embodiment, further comprising: assigning a distinct radiofrequency to each pixel in a row of pixels.

17. A method as recited in any previous embodiment, further comprising: generating an image of the sample from the detected fluorescence emissions.

18. A method as recited in any previous embodiment, wherein the image generation comprises: applying a Fast Fourier Transform to a reference comb to identify comb-line frequencies; dividing a received signal into frames; applying a Fast Fourier Transform to the divided signal; recording values of transformed signal at comb-line frequencies; and forming an image from the recorded values.

19. A method as recited in any previous embodiment, wherein the image generation comprises: obtaining a signal from the detector; calculating comb tones; mixing the signal with each comb tone to produce a mixed signal; passing the signal through a low pass filter to determine temporal resolution; undersampling the filtered signal; and forming an image.

20. A method as recited in any previous embodiment, wherein the image generation comprises: obtaining a signal from the detector; calculating comb tones; mixing the signal with each comb tone to produce a mixed signal; passing each comb tone of the signal through a digital low pass filter in parallel; oversampling the filtered signals; and forming an image.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of fluorescence imaging, the method comprising:
   (a) creating a first beam of frequency shifted light;
   (b) creating a second beam of frequency shifted light;
   (c) interrogating a sample with the first and second beams of light; and
   (d) detecting a response in the sample from exposure to the beams of frequency shifted light;
   (e) applying a Fast Fourier Transform to a reference comb to identify comb-line frequencies;
   (f) dividing a received signal into frames;
   (g) applying a Fast Fourier Transform to the divided signal;
   (h) recording values of transformed signal at comb-line frequencies; and
   (i) forming an image from the recorded values.

2. The method as recited in claim 1, further comprising:
   combining the first beam and the second beam to produce a combined beam; and
   interrogating the sample with the combined beam.

3. The method as recited in claim 1, wherein said first beam is created with an acousto-optic deflector driven by an RF comb and an excitation laser beam.

4. The method as recited in claim 1, wherein said second beam is created with an acousto-optic frequency shifter driven by an RF tone and an excitation laser beam.

5. The method as recited in claim 1, further comprising:
   assigning a distinct radiofrequency to each pixel in a row of pixels.

6. A method of fluorescence imaging, the method comprising:
   (a) creating a first beam of frequency shifted light;
   (b) creating a second beam of frequency shifted light;
   (c) interrogating a sample with the first and second beams of light;
   (d) detecting a response in the sample from exposure to the beams of frequency shifted light;
   (e) obtaining a signal from the detector;
   (f) calculating comb tones;
   (g) mixing the signal with each comb tone to produce a mixed signal;
   (h) passing the signal through a low pass filter to determine temporal resolution;
   (i) undersampling the filtered signal; and
   (j) forming an image.

7. The method as recited in claim 6, further comprising:
   combining the first beam and the second beam to produce a combined beam; and
   interrogating the sample with the combined beam.

8. The method as recited in claim 6, wherein said first beam is created with an acousto-optic deflector driven by an RF comb and an excitation laser beam.

9. The method as recited in claim 6, wherein said second beam is created with an acousto-optic frequency shifter driven by an RF tone and an excitation laser beam.

10. The method as recited in claim 6, further comprising:
    assigning a distinct radiofrequency to each pixel in a row of pixels.

11. A method of fluorescence imaging, the method comprising:
    (a) creating a first beam of frequency shifted light;
    (b) creating a second beam of frequency shifted light;
    (c) interrogating a sample with the first and second beams of light;

(d) detecting a response in the sample from exposure to the beams of frequency shifted light;
(e) obtaining a signal from the detector;
(f) calculating comb tones;
(g) mixing the signal with each comb tone to produce a mixed signal;
(h) passing each comb tone of the signal through a digital low pass filter in parallel;
(i) oversampling the filtered signals; and
(j) forming an image.

12. The method as recited in claim 11, further comprising:
combining the first beam and the second beam to produce a combined beam; and
interrogating the sample with the combined beam.

13. The method as recited in claim 11, wherein said first beam is created with an acousto-optic deflector driven by an RF comb and an excitation laser beam.

14. The method as recited in claim 11, wherein said second beam is created with an acousto-optic frequency shifter driven by an RF tone and an excitation laser beam.

15. The method as recited in claim 11, further comprising:
assigning a distinct radiofrequency to each pixel in a row of pixels.

\* \* \* \* \*